US012667250B2

(12) United States Patent  
Landes et al.

(10) Patent No.: US 12,667,250 B2  
(45) Date of Patent: Jun. 30, 2026

(54) ENDOSCOPIC SPECTRAL ILLUMINATION DEVICE HAVING LEDS EMITTING DIFFERENT WAVELENGTHS OF LIGHT

(71) Applicant: HOYA CORPORATION, Tokyo (JP)

(72) Inventors: Hermann Landes, Friedberg (DE);  
Thomas Viebach, Friedberg (DE)

(73) Assignee: HOYA CORPORATION, Tokyo (JP)

( * ) Notice: Subject to any disclaimer, the term of this patent is extended or adjusted under 35 U.S.C. 154(b) by 420 days.

(21) Appl. No.: 18/268,449

(22) PCT Filed: Dec. 13, 2021

(86) PCT No.: PCT/IB2021/061621  
§ 371 (c)(1),  
(2) Date: Jun. 20, 2023

(87) PCT Pub. No.: WO2022/137005  
PCT Pub. Date: Jun. 30, 2022

(65) Prior Publication Data  
US 2024/0032782 A1 Feb. 1, 2024

(30) Foreign Application Priority Data  
Dec. 21, 2020 (DE) ..................... 10 2020 134 332.9

(51) Int. Cl.  
*A61B 1/06* (2006.01)  
*A61B 1/04* (2006.01)  
*A61B 1/07* (2006.01)

(52) U.S. Cl.  
CPC .......... *A61B 1/0638* (2013.01); *A61B 1/0607* (2013.01); *A61B 1/063* (2013.01);  
(Continued)

(58) Field of Classification Search  
None  
See application file for complete search history.

(56) References Cited

U.S. PATENT DOCUMENTS 6,217,512 B1 * 4/2001 Salo ..................... A61B 1/0607  
600/179  
6,331,156 B1 * 12/2001 Haefele ................... A61B 1/07  
600/179  
(Continued)

FOREIGN PATENT DOCUMENTS

CN 101052341 A 10/2007  
CN 102038482 A 5/2011  
(Continued)

OTHER PUBLICATIONS

Office Action issued in Japanese Patent Application No. 2023-508077, dated Mar. 12, 2024, along with an English translation thereof.

(Continued)

*Primary Examiner* — John P Leubecker  
(74) *Attorney, Agent, or Firm* — Greenblum & Bernstein, P.L.C.

(57) ABSTRACT

Provided is an endoscope tip or capsule endoscope comprising an illumination device configured to illuminate a scene; wherein the illumination device includes a first light source configured to emit light with a first spectral distribution and a second light source configured to emit light with a second spectral distribution;

the first spectral distribution is different from the second spectral distribution;

a clearance between the first light source and the second light source is smaller than twice a dimension among the dimensions of the first light source and the dimensions of the second light source;

the clearance between the first light source and the second light source indicates the length of a shortest straight (Continued)

line segment which connects a point on the first light source with a point on the second light source.

23 Claims, 11 Drawing Sheets

(52) U.S. Cl.
CPC .......... *A61B 1/0655* (2022.02); *A61B 1/0684* (2013.01); *A61B 1/07* (2013.01); *A61B 1/041* (2013.01); *A61B 1/0676* (2013.01)

(56) References Cited

U.S. PATENT DOCUMENTS

| | | | | |
|---|---|---|---|---|
| 7,629,570 | B2* | 12/2009 | Mondloch | F21V 29/89 |
| | | | | 250/227.11 |
| 7,983,458 | B2* | 7/2011 | Wang | H04N 19/172 |
| | | | | 348/700 |
| 10,111,577 | B2* | 10/2018 | Weber | A61B 1/12 |
| 11,627,871 | B2 | 4/2023 | Weber et al. | |
| 2002/0193664 | A1* | 12/2002 | Ross | A61B 1/0607 |
| | | | | 600/179 |
| 2003/0028078 | A1* | 2/2003 | Glukhovsky | A61B 1/0676 |
| | | | | 600/109 |
| 2003/0060702 | A1* | 3/2003 | Kuth | A61B 1/041 |
| | | | | 600/9 |
| 2003/0073935 | A1* | 4/2003 | Segawa | A61B 1/042 |
| | | | | 600/593 |
| 2003/0125788 | A1* | 7/2003 | Long | A61B 1/00094 |
| | | | | 607/133 |
| 2004/0092794 | A1* | 5/2004 | Chin | A61B 1/00071 |
| | | | | 600/179 |
| 2005/0215911 | A1* | 9/2005 | Alfano | A61B 1/041 |
| | | | | 600/476 |
| 2005/0267328 | A1* | 12/2005 | Blumzvig | G02B 13/0065 |
| | | | | 348/E5.029 |
| 2005/0277808 | A1* | 12/2005 | Sonnenschein | A61B 1/053 |
| | | | | 600/153 |
| 2006/0183977 | A1* | 8/2006 | Ishigami | A61B 1/0684 |
| | | | | 600/179 |
| 2006/0215406 | A1 | 9/2006 | Thrailkill | |
| 2006/0293565 | A1* | 12/2006 | Uchimura | A61B 1/00121 |
| | | | | 600/179 |
| 2007/0173695 | A1* | 7/2007 | Hirata | G02B 23/2461 |
| | | | | 600/152 |
| 2008/0139881 | A1* | 6/2008 | Cover | H04N 7/185 |
| | | | | 600/103 |
| 2008/0239070 | A1* | 10/2008 | Westwick | A61B 1/0638 |
| | | | | 348/E5.029 |
| 2008/0306470 | A1* | 12/2008 | Friedman | A61B 1/0607 |
| | | | | 606/3 |
| 2009/0016069 | A1* | 1/2009 | McDermott | F21V 5/046 |
| | | | | 362/311.06 |
| 2009/0062605 | A1* | 3/2009 | Orihara | A61B 1/0607 |
| | | | | 600/109 |
| 2009/0159912 | A1* | 6/2009 | Engl | F21S 41/16 |
| | | | | 257/E33.001 |
| 2009/0306474 | A1* | 12/2009 | Wilson | A61B 1/0661 |
| | | | | 600/109 |
| 2009/0312618 | A1* | 12/2009 | Hengerer | A61B 34/73 |
| | | | | 600/476 |
| 2010/0016662 | A1* | 1/2010 | Salsman | A61B 1/0676 |
| | | | | 600/109 |

| | | | | |
|---|---|---|---|---|
| 2010/0137682 | A1* | 6/2010 | Doguchi | A61B 1/0646 |
| | | | | 600/168 |
| 2010/0286475 | A1* | 11/2010 | Robertson | A61B 1/00188 |
| | | | | 600/109 |
| 2010/0292534 | A1* | 11/2010 | Minai | A61B 1/0605 |
| | | | | 600/109 |
| 2011/0065987 | A1* | 3/2011 | Mullick | A61B 1/126 |
| | | | | 600/109 |
| 2011/0115891 | A1* | 5/2011 | Trusty | A61B 1/00029 |
| | | | | 307/104 |
| 2011/0172492 | A1 | 7/2011 | Erikawa | |
| 2011/0207998 | A1* | 8/2011 | Katayama | A61B 1/041 |
| | | | | 600/106 |
| 2012/0010465 | A1 | 1/2012 | Erikawa et al. | |
| 2013/0231536 | A1* | 9/2013 | Pascal | A61B 1/0638 |
| | | | | 600/178 |
| 2013/0281845 | A1* | 10/2013 | Luiken | A61B 5/0071 |
| | | | | 600/431 |
| 2014/0085891 | A1* | 3/2014 | Takahara | H05K 1/111 |
| | | | | 362/249.01 |
| 2015/0016142 | A1* | 1/2015 | Chang | A61B 1/00 |
| | | | | 362/583 |
| 2016/0249793 | A1* | 9/2016 | Wang | A61B 5/073 |
| | | | | 600/109 |
| 2017/0014020 | A1* | 1/2017 | Tseng | A61B 1/00114 |
| 2018/0055338 | A1* | 3/2018 | Wei | A61B 1/00103 |
| 2019/0167085 | A1 | 6/2019 | Wilson | |
| 2019/0216325 | A1* | 7/2019 | Ouyang | G02B 23/2461 |
| 2020/0113424 | A1* | 4/2020 | Griffin | G06N 3/045 |
| 2020/0154043 | A1* | 5/2020 | Cogal | A61B 1/045 |
| 2020/0287110 | A1* | 9/2020 | Oh | H10H 20/01 |
| 2021/0112647 | A1* | 4/2021 | Coleman | G01S 17/42 |
| 2022/0151550 | A1* | 5/2022 | Zhou | A61B 1/267 |
| 2023/0218153 | A1* | 7/2023 | Liu | H01L 25/0753 |
| | | | | 359/601 |

FOREIGN PATENT DOCUMENTS

| | | |
|---|---|---|
| CN | 102119846 A | 7/2011 |
| CN | 102309307 A | 1/2012 |
| CN | 104224094 A | 12/2014 |
| DE | 102018202243 A1 | 8/2019 |
| JP | 2007-068990 A | 3/2007 |
| JP | 2007-139822 A | 6/2007 |
| JP | 2010-233857 A | 10/2010 |
| JP | 2011-083617 A | 4/2011 |
| JP | 2011-133662 A | 7/2011 |
| JP | 2011-156339 A | 8/2011 |
| JP | 2012-016545 A | 1/2012 |
| WO | 2008/016195 A1 | 2/2008 |

OTHER PUBLICATIONS

First Office Action issued in Chinese Patent Application No. 202180083412.4, dated Jul. 25, 2025, along with an English translation thereof.

Office Action issued in European patent application No. 21827666.5, dated Jul. 18, 2025.

U.S. Appl. No. 18/023,510 to Hermann LANDES, which was filed on Feb. 27, 2023.

International Search Report issued in International Bureau of WIPO Patent Application No. PCT/IB2021/061621, dated Mar. 15, 2022, along with an English translation thereof.

\* cited by examiner

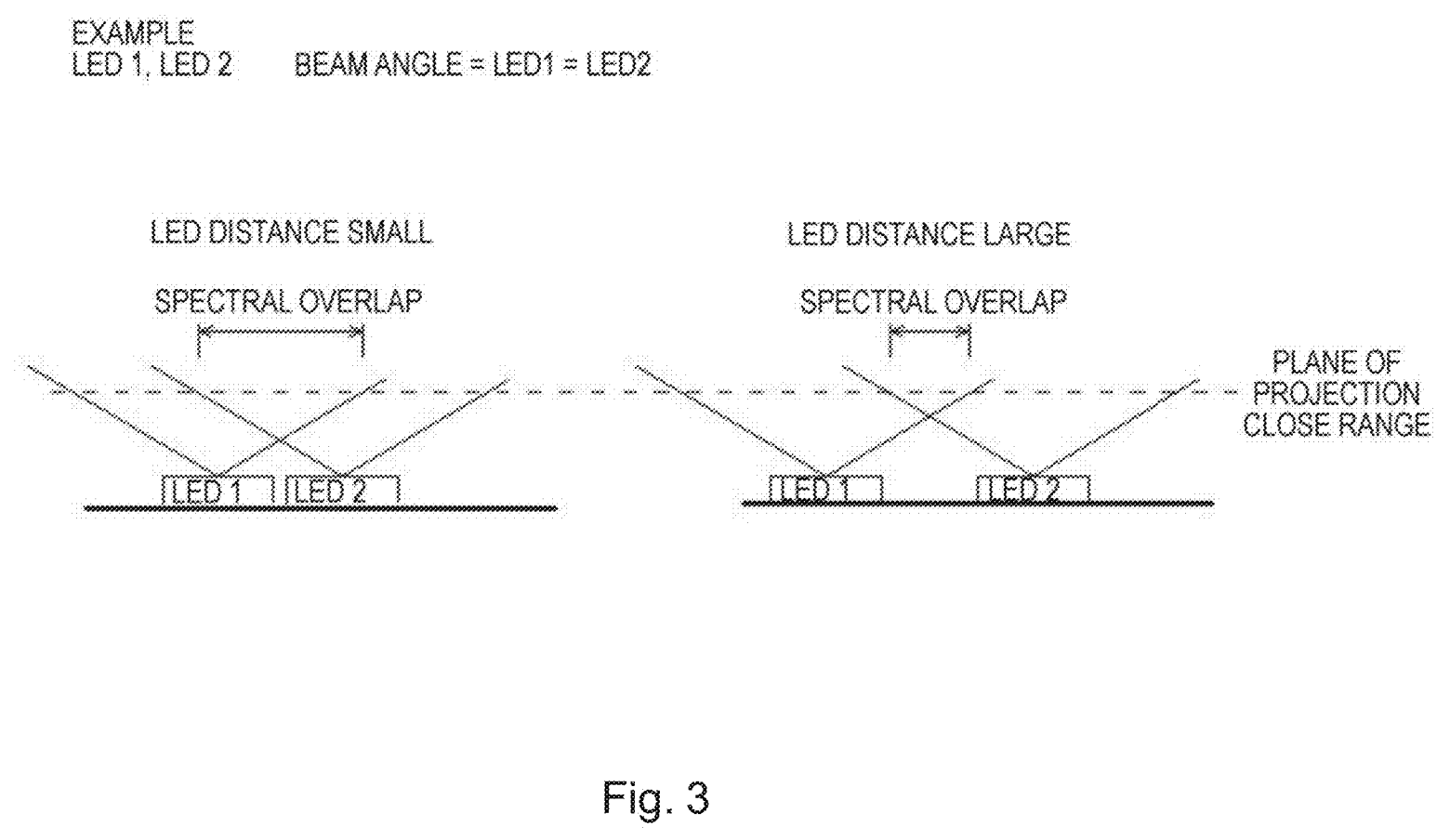

EXAMPLE
LED 1, LED 2    BEAM ANGLE = LED1 = LED2

LED DISTANCE SMALL

SPECTRAL OVERLAP

LED 1    LED 2

LED DISTANCE LARGE

SPECTRAL OVERLAP

LED 1    LED 2

PLANE OF
PROJECTION
CLOSE RANGE

Fig. 3

PLAN VIEW OF
ENDOSCOPE TIP

ENDOSCOPIC SPECTRAL ILLUMINATION DEVICE HAVING LEDS EMITTING DIFFERENT WAVELENGTHS OF LIGHT

The present invention relates to an illumination device as may be used in endoscopes, for example for spectral illumination. For example, spectral illumination may be produced by different types of LEDs.

PRIOR ART

LED illumination with different wavelengths improves the detectability of certain structures in the endoscope image. For example, the structure of blood vessels can be better recognized by illuminating with ultraviolet or violet light in a wavelength range between 380 nm and 450 nm (further referred to as UV light) and green light in a wavelength range around 650 nm (enhanced vascular imaging).

For this purpose, the endoscope tip contains an illumination device capable of emitting UV light and green light, and an imaging device (objective lens) capable of imaging an image of the illuminated scene onto a surface.

SUMMARY OF THE INVENTION

Provided is an endoscope tip or capsule endoscope comprising an illumination device configured to illuminate a scene; wherein the illumination device includes several groups of light sources;

each of the groups includes a respective first light source configured to emit light with a first spectral distribution, and a respective second light source configured to emit light with a second spectral distribution;

the first spectral distribution is different from the second spectral distribution;

for each of the groups and for each two light sources A and B selected from the first light source of the respective group, the second light source of the respective group, the first light source of the group adjacent to the respective group, and the second light source of the group adjacent to the respective group, a clearance between the light sources A and B indicates a length of a shortest straight line segment which connects a point on the light source A with a point on the light source B; and at least one of the following conditions is satisfied:

for each of the groups the clearance between the first light source of the respective group and the second light source of the respective group is smaller than or equal to the clearance between the first light source of the respective group and the first light source of a group adjacent to the respective group; and for each of the groups the clearance between the first light source of the respective group and the second light source of the respective group is smaller than the clearance between the second light source of the respective group and the second light source of the group that is adjacent to the respective group.

Further provided is an endoscope tip or capsule endoscope comprising an illumination device configured to illuminate a scene; wherein the illumination device includes a first light source configured to emit light with a first spectral distribution and a second light source configured to emit light with a second spectral distribution;

the first spectral distribution is different from the second spectral distribution;

a clearance between the first light source and the second light source is smaller than twice a dimension among the dimensions of the first light source and the dimensions of the second light source;

the clearance between the first light source and the second light source indicates the length of a shortest straight line segment which connects a point on the first light source with a point on the second light source.

These endoscope tips or capsule endoscopes allow for optimal color mixing and uniform illumination of the scene with the mixed light.

BRIEF DESCRIPTION OF THE DRAWINGS

FIG. 3 shows how color mixing at close range is improved by arranging the LEDs in an endoscope tip according to some embodiments of the invention;

DESCRIPTION OF SOME EMBODIMENTS

Figure 1:
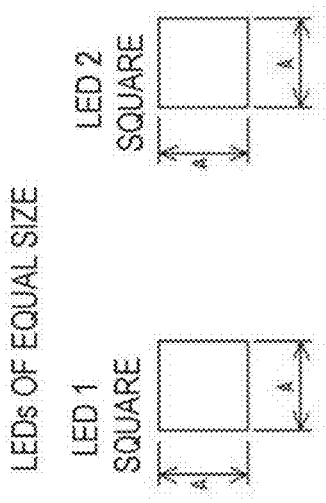
FIG. 1 shows how two LEDs of equal size are disposed in an endoscope tip according to some embodiments of the invention.
Figure 1:
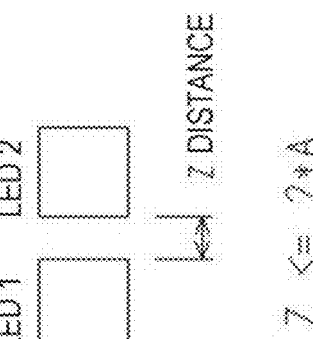

In the following, some embodiments of the invention are explained with reference to the accompanying drawings. However, these embodiments are not limiting.

The invention relates to an endoscope tip. The endoscope tip may be used alone (so-called capsule endoscopy), or it may be part of an endoscope. In the latter case, the endoscope also has a rigid shaft (pipe) or a flexible shaft (tube). A proximal end of the endoscope tip is connected to the distal end of the shaft. In some embodiments, an angulation segment is located between the distal end of the shaft and the proximal end of the endoscope tip, such that the endoscope tip is only indirectly connected to the shaft. In other embodiments, the endoscope tip is directly connected to the shaft.

The endoscope tip or endoscope may be suitable for insertion into a cavity (e.g. a cavity of a human body). The endoscope may be, for example, a bronchoscope, a laryngoscope, or a colonoscope.

The endoscope tip has an illumination device. The illumination device serves to illuminate a scene located in front of and/or adjacent to the endoscope tip, in particular the distal end of the endoscope tip. Accordingly, the illumination device is located at or near the distal end of the endoscope tip. The illumination may serve to allow that an imaging device located in the endoscope tip images the scene onto a surface where it may be observed. The surface may be inside or outside the endoscope tip, and may have an image sensor attached thereto, for example. However, the illumination can also be therapeutic, for example in photo-immunotherapy. In this case, the scene can be imaged and observed either by an imaging device in the same endoscope tip or by an imaging device in a second endoscope.

In particular, the invention may be applied in an endoscope having a wide-angle lens. For example, the wide-angle lens may have a view angle (Field of View) of 180° or more, preferably 220° or more, and further preferably 230° or more.

The illumination device includes a first light source and a second light source. The first light source is configured to emit light with a first spectral distribution. The second light source is configured to emit light with a second spectral distribution. The first spectral distribution is different from the second spectral distribution. The peak wavelengths of the first and second spectral distributions are not particularly limited. Each of them can be, for example, in the visible range (about 400 nm to 800 nm), in the ultraviolet range (<400 nm), or in the infrared range (>800 nm).

The light sources are typically LEDs. However, they can also be laser diodes. Furthermore, they can be emission ends of light guides with corresponding light emission devices (e.g. lasers) at their input end, wherein for the geometrical considerations in the present application the emission ends from the light guides are considered to be the light sources. In the latter case, the light emission devices may be located at the proximal end of the endoscope, or they may be located at the proximal end of the endoscope tip. However, they may also be located outside the endoscope, wherein light guides transmit the light from the light emission devices to the proximal end of the endoscope and from there to the distal end or near the distal end of the endoscope so that the scene is illuminated.

In some embodiments (e.g. for enhanced vascular imaging), it is particularly desired that the scene be illuminated uniformly by both light sources, with no major color differences. In such embodiments, for example, the first and second light sources may be electrically connected in parallel or in series so that they are always either switched on or switched off simultaneously. However, the endoscope tip or endoscope may also comprise a control device that can control the first light source together with, and possibly separately from, the second light source. Controlling means at least switching on and off, but may also include controlling the intensity of the light or the color of the light.

Conventionally, the first and second light sources are disposed with sufficient clearance from each other to allow for an assembly as easy as possible. However, according to some embodiments of the invention, the first and second light sources are preferably disposed close to each other. In particular, they are preferably disposed such that their clearance from each other is smaller than twice a dimension among the dimensions of the light sources perpendicular to their clearance. The clearance between a light source A and a light source B denotes the length of the shortest straight line segment that exists between a point on the light source A and a point on the light source B.

The term "dimension of the light source" means, for a given direction, the longest dimension of the light source parallel to the given direction. For a square light source, the shortest dimension of the light source's dimensions is the edge length of the square and the longest dimension of the light source's dimensions is the diagonal of the square. For a rectangular light source, the shortest dimension of the light source's dimensions is the shorter edge length of the rectangle and the longest dimension of the light source's dimensions is the diagonal of the rectangle. For a circular light source, the shortest and the longest dimension of the light source's dimensions is the diameter of the light source. For a light source with an elliptical shape, the shortest dimension of the light source's dimensions is the length of the shorter axis of the ellipse, and the longest dimension of the light source's dimensions is the long axis of the ellipse.

The dimension whose double is greater than or equal to the clearance of the light sources may be, for example, the smallest of the dimensions of the two light sources perpendicular to the straight line segment defining the clearance, the largest of the dimensions of the two light sources perpendicular to the straight line segment defining the clearance, or the average of the smallest of the two dimensions and the largest of the two dimensions perpendicular to the straight line segment defining the clearance.

Figure 2:
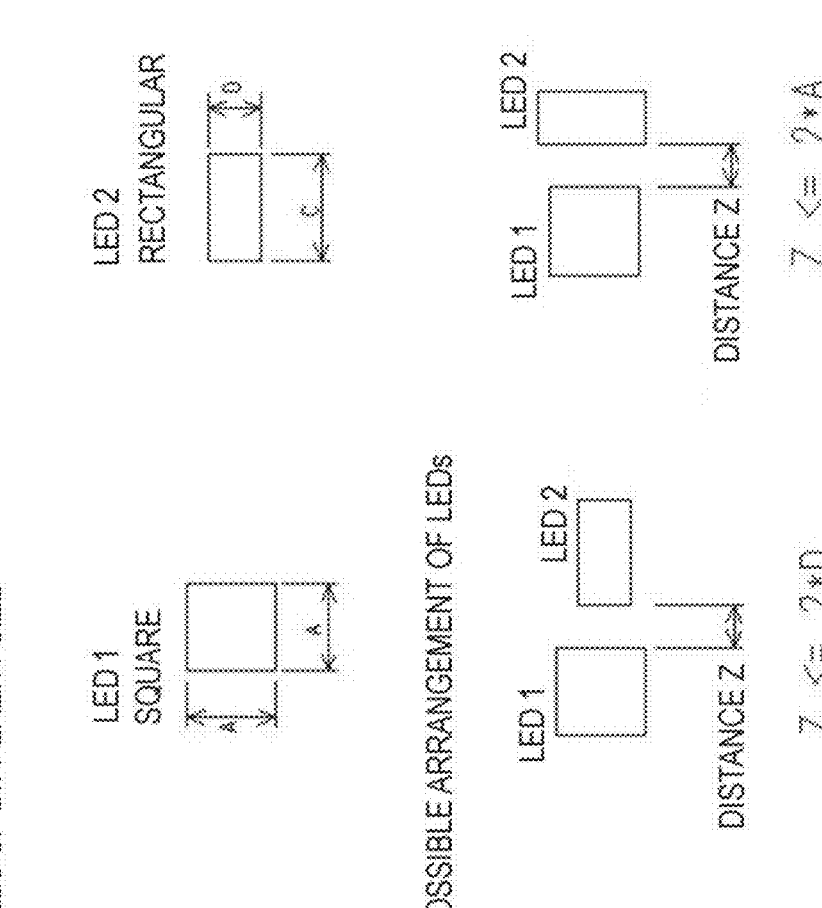
FIG. 2 shows how two LEDs of different size are disposed in an endoscope tip according to some embodiments of the invention.

Preferred arrangements of the first and second light sources are shown in FIGS. 1 and 2 for the example of square light sources (FIG. 1) and the example of rectangular light sources (FIG. 2) for the case where the relevant dimension is the smallest of the dimensions of the two light sources. In FIG. 1, the two square LED 1 (first light source) and LED 2 (second light source) with an edge length A are disposed such that their clearance Z is $\leq 2*A$. FIG. 2 shows two ways in which a rectangular LED 2 with edge lengths D and C can be disposed relative to a square LED 1 with edge length A in an endoscope tip according to some embodiments of the invention, with D<A<C applying here. When the shortest straight line segment between a point on the square LED 1 and a point on the rectangular LED 2 (i.e., their clearance) is in the longitudinal direction of the LED 2 (left in FIG. 2), the clearance Z between the LEDs is $Z \leq 2*D$ because D is the smaller dimension perpendicular to the shortest straight line segment. When the shortest straight line segment between a point on the square LED 1 and a point on the rectangular LED 2 (i.e., their clearance) is in the transverse direction of the LED 2 (right in FIG. 2), the clearance Z between the LEDs is $Z \leq 2*A$ because A is the smaller dimension perpendicular to the shortest straight line segment.

In addition, it is occasionally preferred that a distance between the light sources be particularly short, e.g. smaller than three times or twice a dimension of the light sources, wherein the dimension may be as defined above. The distance indicates the length of the straight line segment connecting the barycenters of the light emissions of the two light sources. Generally, the barycenters of the light emission correspond to the geometric centers of the light emitting surfaces. If the barycenter of the light emission should change depending on a parameter (e.g. voltage or temperature), the barycenter of the light emission is chosen at the maximum light emission of the respective light source.

Preferably, the straight line segment that determines the clearance is parallel to the straight line segment that determines the distance. Thus, if other geometric constraints do not speak against it, a particularly compact form of the group comprising the first and second LEDs can be achieved. This feature is fulfilled in the example of FIG. 2 (left), but not in the example of FIG. 2 (right). Instead, in the example of FIG. 2 (right), the lower edges of LEDs 1 and 2 are in a line, so that the lower edge length (an edge length parallel to the shortest straight line segment) of this group of the first and second LEDs is minimized.

Instead of the factor 2 in the inequalities above, this factor can preferably be 1.5 or even only 1.

A lower limit of the clearance is set by the possibility of mounting the two LEDs (e.g. soldering them on a circuit board). For example, the clearance Z may be greater than 0.3 times or greater than 0.5 times the shortest dimension among the dimensions of the light sources perpendicular to the straight line segment defining the clearance.

FIG. 3 illustrates that the smaller the distance or clearance between the two LEDs, the better the spectral overlap of the two lights emitted by the LEDs. This is particularly relevant at close range; at greater distances of the illuminated scene, the relevance of the distance or clearance of the light sources from each other becomes smaller.

In some embodiments of the invention, the illumination device has multiple groups of light sources. In each group, there is at least a first light source and a second light source corresponding to the first and second light sources described above. Conventionally, these light sources are mounted such that their mutual clearances are approximately equal. This makes mounting (e.g. soldering on a circuit board) easier.

However, according to some embodiments of the invention, for each of the groups, the clearance between the first light source and the second light source of the group is smaller than the clearance between a first or second light source of the respective group and a corresponding light source of an adjacent group. For example, it is smaller than the clearance between the first or second light source of the respective group and the corresponding light source of the adjacent group by at least 20%, more preferably by at least 40%, and even more preferably by at least 60%. Within each group, the first and second light sources preferably have a clearance that is smaller than or equal to the maximum clearance described above for the case of a single first light source and a single second light source.

The clearances between the first light sources of adjacent groups may be equal or unequal to the clearances between the second light sources of the adjacent groups. When the clearances are unequal, it is sufficient that the clearance between the first and second light sources in the group is smaller than the larger one of the two clearances between corresponding light sources of the groups, but it is preferred that it is smaller than both clearances between corresponding light sources of the groups.

Accordingly, it is preferred that the clearance between the first and second light sources of each group is smaller than the clearance between the first light source of one group and the second (i.e. the other) light source of the adjacent group. Preferably, the same is true for the clearance between the second light source of one group and the first (i.e. the other) light source of the adjacent group.

In preferred embodiments, the above considerations for the clearance between light sources of the same group and light sources of adjacent groups apply mutatis mutandis to the clearances between the light sources of the same group and the light sources of adjacent groups.

The groups may be disposed along a line, wherein the line may be straight or curved (e.g. a circular segment). The line can be closed to a circle, an ellipse, or a polygon (triangle, square, rectangle, . . . ). For example, if the closed shape is a circle, it is sufficient if only the first light source (or only the second light source) is disposed on the circle for each group, but in some embodiments both the first light source and the second light source may be disposed on the circle.

Preferably, the two circles (or circular segments) have a common center. Preferably, the circles (or circular segments) are disposed around the imaging device. The two circles may also coincide. Preferably, the clearance between corresponding light sources of adjacent groups is the same for all groups, but may be different for various adjacent groups.

Preferably, the clearances between the first and second light sources are the same in each of the groups. Even more preferably, the first and second light sources are disposed equally in each group. For example, when the first light sources are disposed on a circle, an angle between the shortest straight line segment connecting the first light source of the respective group to the second light source of the respective group and a radius from a center of the circle to the first light source of the respective group should be the same preferably for each group. Furthermore, preferably this straight line segment should be the same length for each of the groups.

Such an arrangement makes the mounting (e.g. soldering) of the light sources (e.g. LEDs) more difficult. However, the color mixing is improved.

Figure 4:
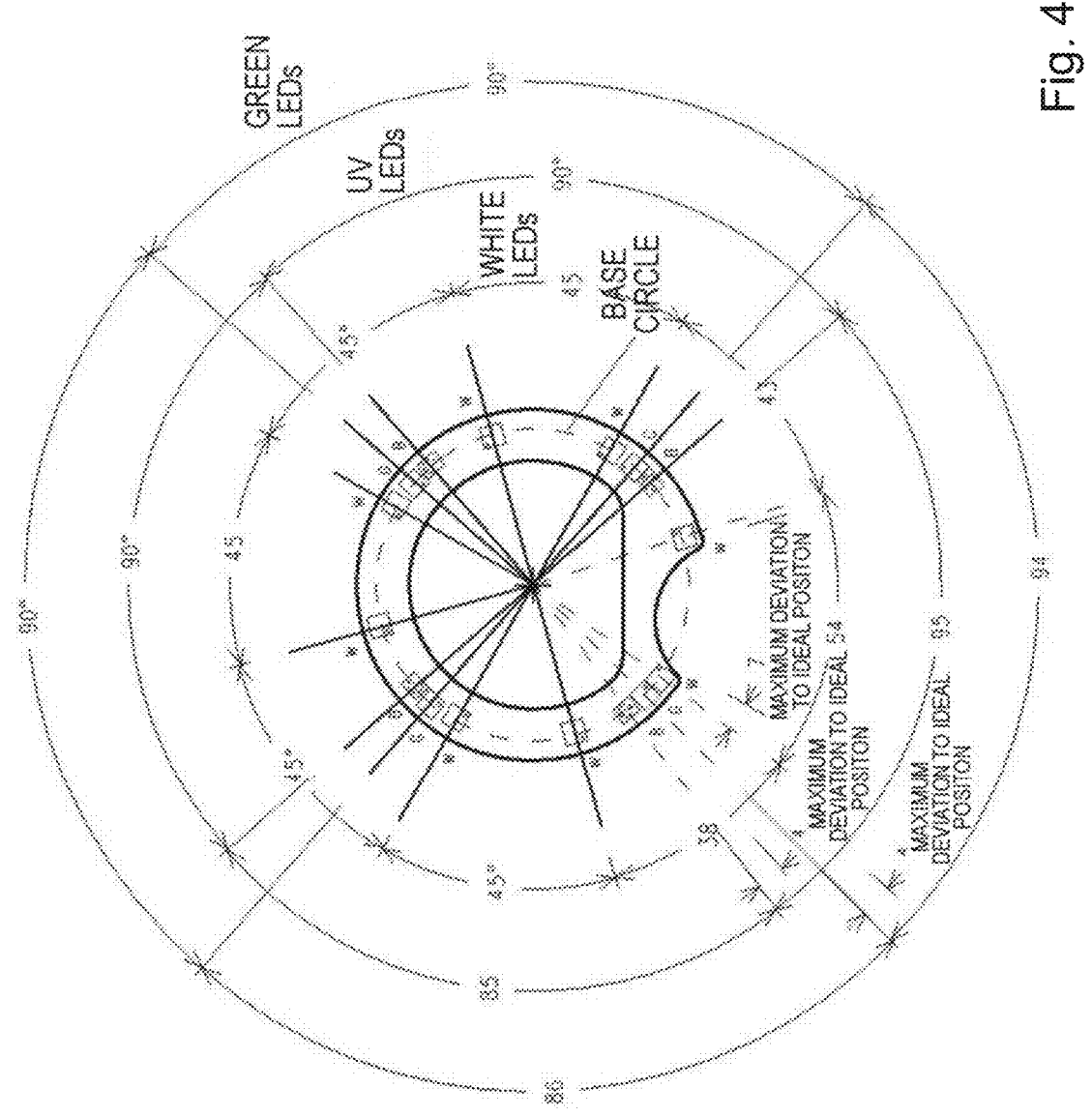
FIG. 4 shows an illumination device that can be used in an endoscope tip according to some embodiments of the invention.

In an embodiment shown in FIG. 4, both the first light sources and the second light sources of the groups are disposed on a circle (or circular segment) around an imaging device (objective lens). The circle is typically concentric with the optical axis of the imaging device. In this embodiment, four groups are disposed, each containing a blue (or UV) LED ("B"; rectangular) and a green LED ("G"; square). In addition, eight white LEDs ("W"; square) are also installed on the circle to also allow the scene to be illuminated with white light. The edge lengths can typically range from 0.1 mm to 0.9 mm.

Preferably, both the groups of blue and green LEDs and the white LEDs should be installed with equal angular distances to each other (i.e. corresponding positions of adjacent groups or LEDs should have a corresponding angular distance on the circle). Such an ideal angle is calculated as 360°/(number of groups or LEDs), i.e. 90° for the four groups and 45° for the eight white LEDs. Then, the corresponding illumination of the scene would be particularly homogeneous, unless additional inhomogeneity is created by the cap geometry at the distal end of the endoscope tip.

Figure 5:
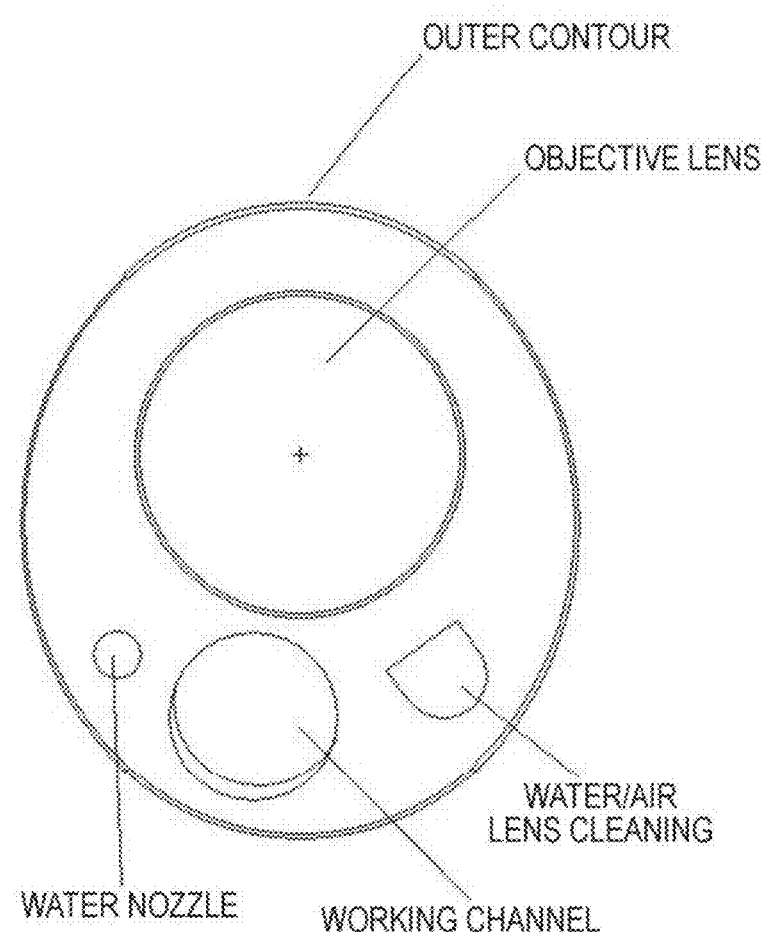
FIG. 5 shows a plan view of an endoscope tip including the illumination device of FIG. 4, according to some embodiments of the invention.
Figure 6:
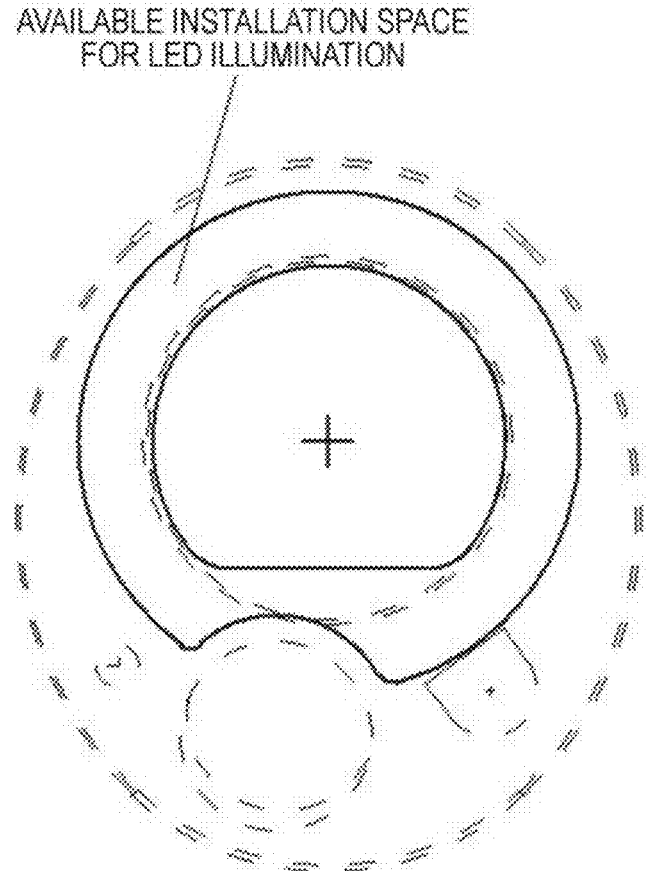
FIG. 6 indicates the space available for the illumination device in the plan view of the endoscope tip of FIG. 5.
Figure 7:
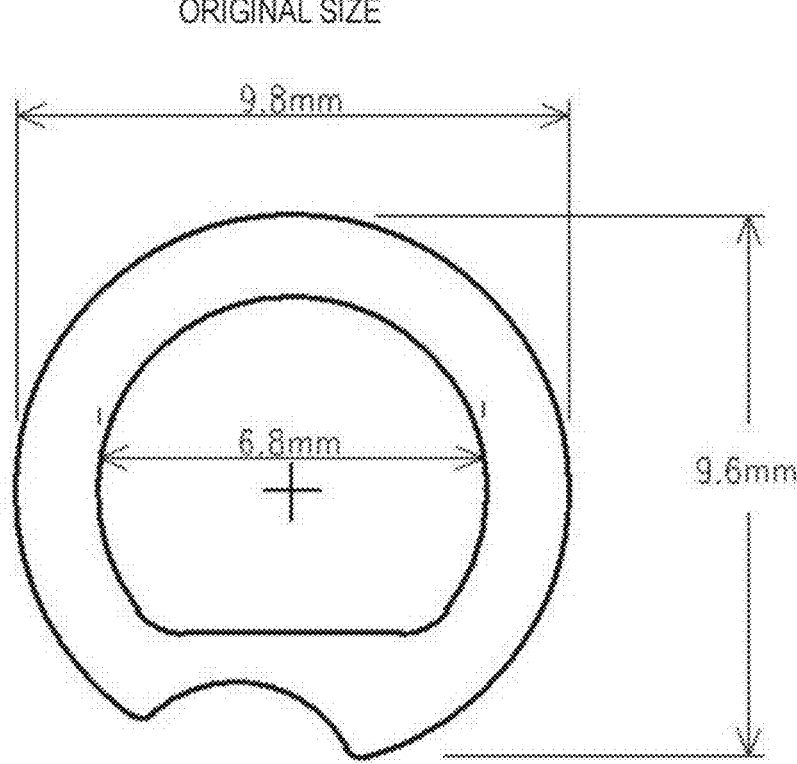
FIG. 7 indicates the dimensions of the space available for the illumination device in the plan view of the endoscope tip of FIG. 5.

However, it is not always possible to maintain this ideal angle. FIG. 5 shows a plan view of the endoscope tip comprising the illumination device of FIG. 4. As can be seen from FIG. 5, the outlet opening of the working channel is located in the immediate vicinity of the objective lens, so that no LEDs can be mounted in this area. The space available for the illumination device is shown in FIG. 6. The real dimensions of the space available for the illumination device in this example are shown in FIG. 7.

Because of the space occupied by the working channel and in order to dispose not only the groups of one blue and one green LED each, but also the white LEDs as uniformly as possible around the objective lens, a group with one blue and one green LED and one white LED are moved slightly out of the ideal position. In the given example, the angular deviation for the one group is 5.4° (6% of 90°), for the one white LED it is 7.2° (16% of 45°). In general, the deviation should not be greater than 20%, preferably not greater than 15% and even more preferably not greater than 10% of the ideal angle in order to achieve homogeneous illumination of the scene.

The dimensions of the LEDs, the endoscope tip, the working channel, etc. given above are only examples and are not to be interpreted in a restrictive manner.

In other embodiments, the endoscope may even include two or more working channels, and the LEDs or LED groups are moved out of their ideal positions accordingly. In some embodiments, the working channel or working channels may also be disposed such that the LED groups are at their ideal position.

Figure 8A:
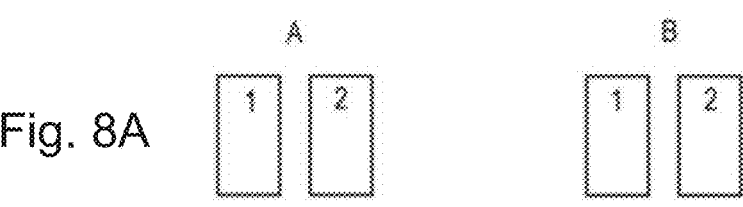
FIGS. 8A through 8K show different arrangement possibilities of two groups each with two different light sources according to some embodiments of the invention.
Figure 8B:
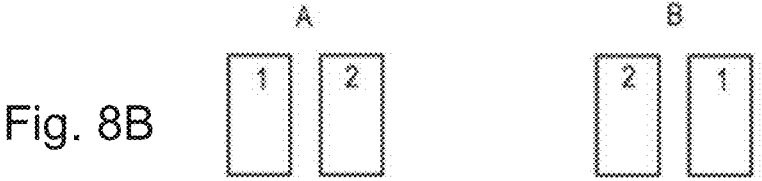
Figure 8C:
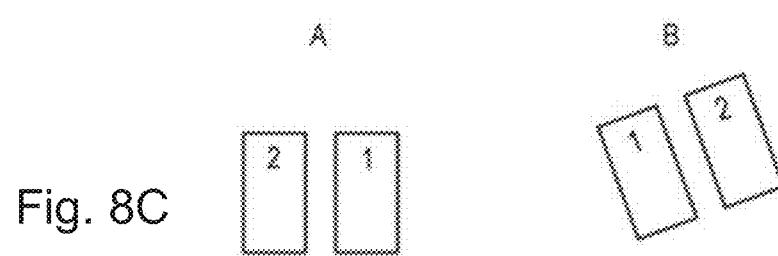
Figure 8D:
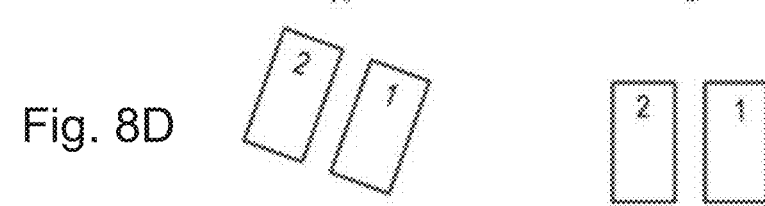
Figures 8E, 8F, 8G, 8H:
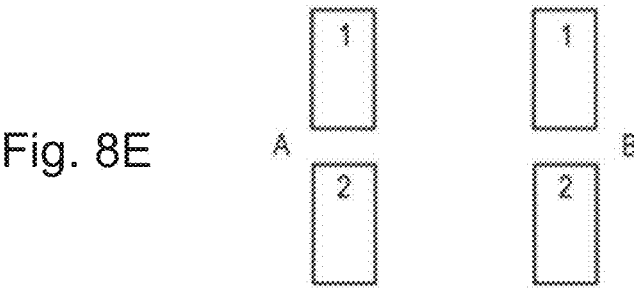
Figure 8I:
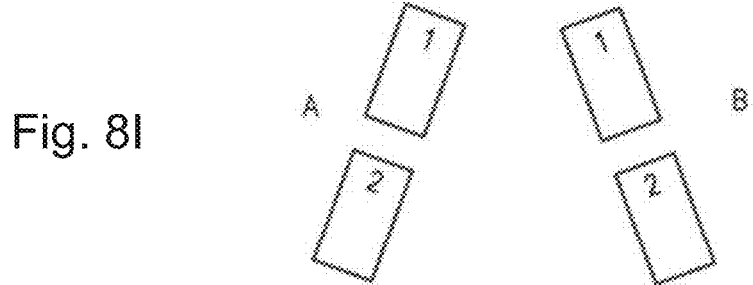
Figure 8J:
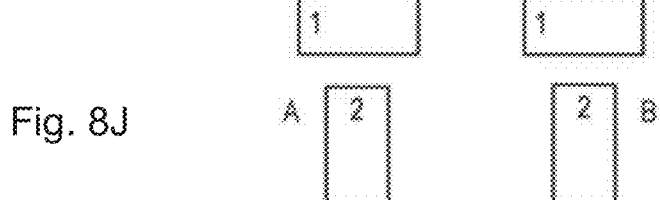
Figure 8K:
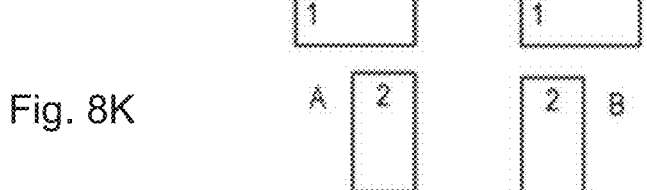
Figures 9A, 9B, 9C, 9D:
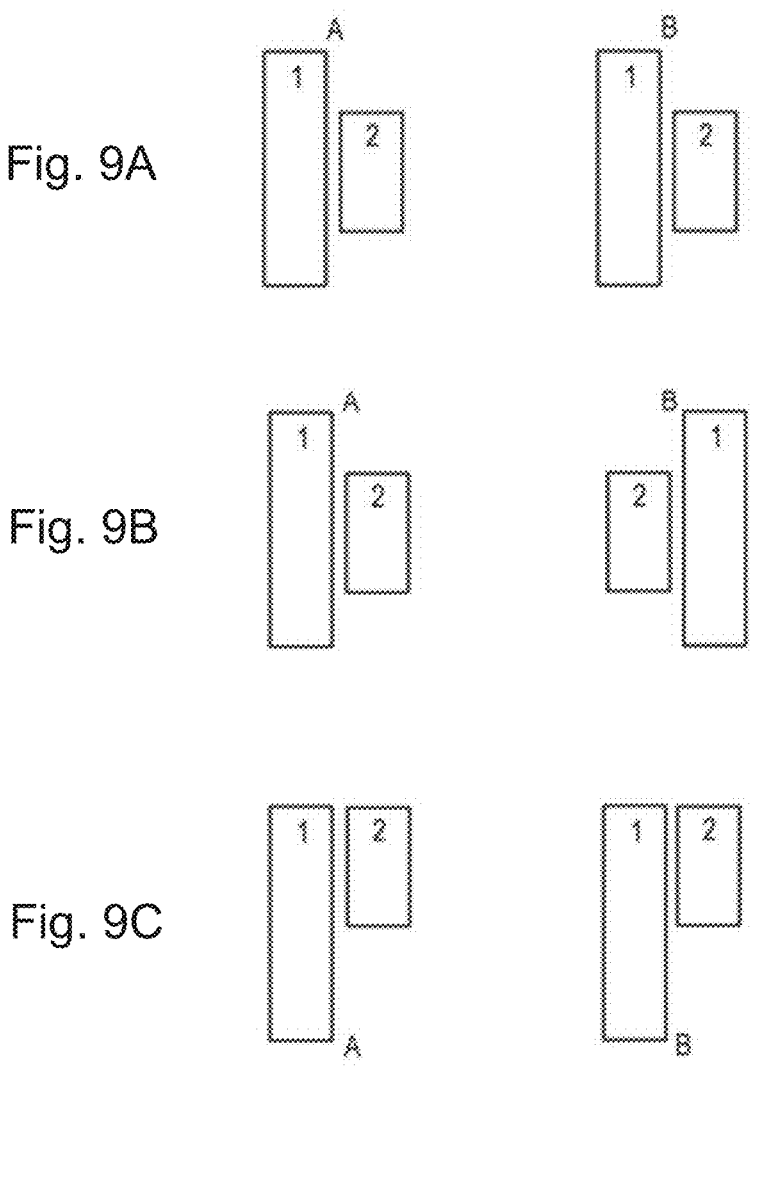
FIGS. 9A through 9D show different arrangement possibilities of two groups each with two different light sources according to some embodiments of the invention.

FIGS. 8 and 9 show some arrangement possibilities of two adjacent groups A and B, each with two different light sources (e.g. LEDs) 1 and 2, according to some embodiments of the invention. In FIG. 8, the two light sources have the same rectangular shape and size; in FIG. 9, they have different sizes.

These arrangement possibilities are not exhaustive. Furthermore, in general, the shape of the light sources is not limited to rectangles, and for rectangles, the ratio of side lengths is arbitrary (including a ratio of 1 (square)). Furthermore, the drawings are not necessarily to scale. Angles that are different from multiples of 90° are shown only as examples. They can be varied as desired.

In all of the examples shown in FIGS. 8 and 9, for each of the groups, the clearance between the first light source of the one group and the second light source of the one group is smaller than or equal to the clearance between the first (or second) light source of the one group and the first (or second) light source of the other group. In the configurations of FIGS. 8*a, b, d, e, f, g, h, j, k* and 9*a, c*, this condition is even fulfilled for both light sources of the one group, accordingly.

In the configurations of FIGS. 8*a, b, e, g, i, j, k* and 9*a, b, c, d* (and, depending on the details, also in the configurations of FIGS. 8*c, d, f, h*), the clearance between the first light source of the one group and the second light source of the one group is smaller than or equal to the clearance between the first light source (or the second light source) of the one group and the second light source (or the first light source) of the other group. In the configurations of FIGS. 8*a, e, g, i, j, k* and 9*d* (and, depending on details, also in the configurations of FIGS. 8*b, c, d, f, h*; 9*a, b*), this condition is even fulfilled for both light sources of the one group, accordingly.

In the configurations of FIGS. 8*a, b, c, d, f, g, h, i, j* and 9*a, b, d* (and, depending on details, also in the configurations of FIGS. 8*k*; 9*c*), the distance between the first light source of the one group and the second light source of the one group is smaller than or equal to the distance between the first light source (or the second light source) of the one group and the first light source (or the second light source) of the other group. In the configurations of FIGS. 8*a, b, c, d, f, h, j,* and 9*a* (and, depending on the details, also in the configurations of FIGS. 8*g, i, k,* and 9*c*), this condition is even fulfilled for both light sources of the one group, accordingly.

In the configurations of FIGS. 8*a, b, d, e, g, i, j, k* and 9*b, c, d* (and, depending on details, also in the configurations of FIGS. 8*c, f, h* and 9*a*), the distance between the first light source of the one group and the second light source of the one group is smaller than or equal to the distance between the first light source (or the second light source) of the one group and the second light source (or the first light source) of the other group. In the configurations of FIGS. 8*a, b, e, g, i, j, k* and 9*b, d* (and, depending on details, also in the configurations of FIGS. 8*c, f, h* and 9*a, c*), this condition is even fulfilled for both light sources of the one group, accordingly.

The invention claimed is:

1. An endoscope tip or capsule endoscope comprising an illumination device configured to illuminate a scene and including a plurality of groups of light sources, each of the groups of light sources including a respective first light source configured to emit light with a first spectral distribution, and further including a respective second light source configured to emit light with a second spectral distribution;

an optical imaging device configured to image the scene, wherein each of said light sources are arranged in a circular pattern around and at the same radial distance from a center of the optical imaging device; and a working channel outlet configured to accommodate an instrument therethrough, positioned adjacent to the optical imaging device and protruding into a path of the circular pattern such that an area between the working channel outlet and the optical imaging device is free of light sources, wherein:

the first spectral distribution is different from the second spectral distribution;

for each of the groups and for each two light sources A and B selected from the first light source of the respective group, the second light source of the respective group, the first light source of the group adjacent to the respective group, and the second light source of the group adjacent to the respective group, a clearance between the light sources A and B indicates a length of a shortest straight line segment which connects a point on the light source A with a point on the light source B; and at least one of the following conditions is satisfied:

for each of the groups the clearance between the first light source of the respective group and the second light source of the respective group is smaller than or equal to the clearance between the first light source of the respective group and the first light source of a group that is adjacent to the respective group; and for each of the groups the clearance between the first light source of the respective group and the second light source of the respective group is smaller than the clearance between the second light source of the respective group and the second light source of the group that is adjacent to the respective group.

2. The endoscope tip or capsule endoscope according to claim 1, wherein in each of the groups the clearance between the first light source of the respective group and the second light source of the respective group is the same.

3. The endoscope tip or capsule endoscope according to claim 1, wherein in each of the groups the shortest straight line segment between a point of the first light source of the respective group and a point of the second light source of the respective group is smaller than twice a dimension among the dimensions of the first light source of the respective group perpendicular to the shortest straight line segment and the dimensions of the second light source of the respective group perpendicular to the shortest straight line segment.

4. The endoscope tip or capsule endoscope according to claim 1, wherein for each of the groups an edge of the first light source of the respective group and an edge of the second light source of the respective group lie on a line which is parallel to the shortest straight line segment.

5. The endoscope tip or capsule endoscope according claim 1, wherein at least one of the following conditions is satisfied for each of the groups:

the clearance between the first light source of the respective group and the second light source of the respective group is at least 20% smaller than the clearance between the first light source of the respective group and the first light source of the group that is adjacent to the respective group; and the clearance between the first light source of the respective group and the second light source of the respective group is at least 20% smaller than the clearance between the second light source of the respective group and the second light source of the group that is adjacent to the respective group.

6. The endoscope tip or capsule endoscope according to claim 1, wherein at least one of the following conditions is satisfied:

the first light sources are disposed on a first circular segment having a first center around the optical imaging device; and the second light sources are disposed on a second circular segment having a second center around the optical imaging device.

7. The endoscope tip or capsule endoscope according to claim 6, wherein at least one of the following conditions is satisfied:

when the first light sources are disposed on the first circular segment, for each of the groups an angle on the first circular segment between the first light source of the respective group and the first light source of the group adjacent to the respective group deviates from an ideal angle, wherein the deviation from the ideal angle is no more than 20%, and when the second light sources are disposed on the second circular segment, for each of the groups an angle on the second circular segment between the second light source of the respective group and the second light source of the group adjacent to the respective group deviates from the ideal angle, wherein the deviation from the ideal angle is no more than 20%, and the ideal angle is 360° divided by the number of groups.

8. The endoscope tip or capsule endoscope according to claim 6, wherein at least one of the following conditions is satisfied:

when the first light sources are disposed on the first circular segment, an angle between a straight line, which connects a barycenter of a light emission from the first light source of the respective group with a barycenter of a light emission from the second light source of the respective group, and a radius from the first center to the first light source of the respective group is the same in each of the groups, and when the second light sources are disposed on the second circular segment, an angle between a straight line, which connects the barycenter of the light emission from the first light source of the respective group with the barycenter of the light emission from the second light source of the respective group, and a radius from the second center to the second light source of the respective group is the same in each of the groups.

9. The endoscope tip or capsule endoscope according to claim 6, wherein the first center is equal to the second center.

10. The endoscope tip or the capsule endoscope according to claim 6, wherein at least one of the following conditions is satisfied:

a center of a plan view of the optical imaging device is equal to the first center; and the center of the plan view of the optical imaging device is equal to the second center.

11. The endoscope tip or capsule endoscope according to claim 1, wherein at least one of the following conditions is satisfied:

each of the first light sources is a light emitting diode or a laser diode or an emission end of a light guide; and each of the second light sources is a light emitting diode or a laser diode or an emission end of a light guide.

12. The endoscope tip or capsule endoscope according to claim 1, wherein at least one of the following conditions is satisfied:

for each of the groups the clearance between the first light source of the respective group and the second light source of the respective group is smaller than or equal to the clearance between the first light source of the respective group and the second light source of the group that is adjacent to the respective group; and for each of the groups the clearance between the first light source of the respective group and the second light source of the respective group is smaller than or equal to the clearance between the second light source of the respective group and the first light source of the group that is adjacent to the respective group.

13. The endoscope tip or capsule endoscope according to claim 1, wherein for each of the groups the shortest straight line segment between a point on the first light source of the respective group and a point on the second light source of the respective group runs parallel to a straight line segment that connects a barycenter of a light emission from the first light source of the respective group with a barycenter of a light emission from the second light source of the respective group.

14. The endoscope tip or capsule endoscope according to claim 1, wherein for each of the groups and for each two light sources C and D selected from the first light source of the respective group, the second light source of the respective group, the first light source of the group adjacent to the respective group, and the second light source of the group adjacent to the respective group, the distance between the light sources C and D indicates the length of a straight line segment that connects a barycenter of a light emission from the light source C with a barycenter of a light emission from the light source D, and at least one of the following conditions is satisfied:

for each of the groups a distance between the first light source of the respective group and the second light source of the respective group is smaller than or equal to a distance between the first light source of the respective group and the first light source of the group that is adjacent to the respective group; and for each of the groups a distance between the first light source of the respective group and the second light source of the respective group is smaller than or equal to a distance between the second light source of the respective group and the second light source of the group that is adjacent to the respective group.

15. The endoscope tip or capsule endoscope according to claim 1, wherein at least one of the following conditions is satisfied:

for each of the groups the distance between the first light source of the respective group and the second light source of the respective group is smaller than or equal to the distance between the first light source of the respective group and the second light source of the group that is adjacent to the respective group; and for each of the groups the distance between the first light source of the respective group and the second light source of the respective group is smaller than or equal to the distance between the second light source of the respective group and the first light source of the group that is adjacent to the respective group.

16. The endoscope tip or capsule endoscope according to claim 1, wherein in each of the groups the respective first light source is electrically connected in parallel with the respective second light source, or in series with the respective second light source.

17. The endoscope tip or capsule endoscope according to claim 1, further comprising a control unit configured to switch on or off, in each of the groups, the respective first light source together with the respective second light source.

18. An endoscope tip or capsule endoscope comprising an illumination device configured to illuminate a scene and including a plurality of groups of light sources, each of the groups of light sources including a respective first light source configured to emit light with a first spectral distribution and a respective second light source configured to emit light with a second spectral distribution, the first spectral distribution being different from the second spectral distribution;

a lens configured to image the scene, wherein each of said light sources are arranged in a circular pattern around and at the same radial distance from a center of the lens; and a working channel outlet configured to accommodate an instrument therethrough, positioned adjacent to the lens and protruding into a path of the circular pattern such that an area between the working channel outlet and the lens is free of light sources, wherein:

a clearance between the first light source of a respective group and the second light source of the respective group is smaller than twice a dimension among the dimensions of the first light source and the dimensions of the second light source; and the clearance between the first light source of the respective group and the second light source of the respective group indicates the length of a shortest straight line segment which connects a point on the first light source with a point on the second light source.

19. The endoscope tip or capsule endoscope according to claim 18, wherein the dimension among the dimensions of the first light source and the dimensions of the second light source is perpendicular to the shortest straight line segment which connects a point on the first light source with a point on the second light source.

20. The endoscope tip or capsule endoscope according to claim 18, wherein the first light source is electrically connected in parallel with the second light source, or in series with the second light source.

21. The endoscope tip or capsule endoscope according to claim 18, further comprising a control unit configured to switch on or off the first light source together with the second light source.

22. The endoscope tip or capsule endoscope according to claim 18, wherein a distance between the first light source and the second light source is smaller than twice the dimension among the dimensions of the first light source and the dimensions of the second light source; and the distance between the first light source and the second light source indicates the length of a straight line segment which connects a barycenter of a light emission from the first light source with a barycenter of a light emission from the second light source.

23. An endoscope comprising the endoscope tip according to claim 1; and a rigid or flexible shaft that is directly or indirectly connected with the endoscope tip.

\* \* \* \* \*